United States Patent
Opheim

(10) Patent No.: US 11,406,602 B2
(45) Date of Patent: *Aug. 9, 2022

(54) SUBSTANCES FOR REDUCING OCCURRENCE OF MAJOR CARDIAC EVENTS COMPRISING RED YEAST RICE EXTRACT AND OMEGA-3 POLYUNSATURATED FATTY ACID OR DERIVATIVE THEREOF

(71) Applicant: NORDIC NATURALS, INC., Watsonville, CA (US)

(72) Inventor: Joar Opheim, Aptos, CA (US)

(73) Assignee: NORDIC NATURALS, INC., Watsonville, CA (US)

(*) Notice: Subject to any disclaimer, the term of this patent is extended or adjusted under 35 U.S.C. 154(b) by 268 days.

This patent is subject to a terminal disclaimer.

(21) Appl. No.: 16/826,501

(22) Filed: Mar. 23, 2020

(65) Prior Publication Data

US 2020/0281861 A1 Sep. 10, 2020

Related U.S. Application Data

(63) Continuation of application No. 15/870,138, filed on Jan. 12, 2018, now Pat. No. 10,596,121, which is a continuation of application No. 12/630,686, filed on Dec. 3, 2009, now abandoned, which is a continuation-in-part of application No. 11/757,340, filed on Jun. 1, 2007, now abandoned.

(51) Int. Cl.
| | |
|---|---|
| *A61K 9/48* | (2006.01) |
| *A61K 31/20* | (2006.01) |
| *A61K 31/341* | (2006.01) |
| *A61K 31/351* | (2006.01) |
| *A61K 31/355* | (2006.01) |
| *A61K 35/60* | (2006.01) |
| *A61K 36/06* | (2006.01) |
| *A61K 36/88* | (2006.01) |
| *A61K 45/06* | (2006.01) |

(52) U.S. Cl.
CPC ............ *A61K 9/4858* (2013.01); *A61K 31/20* (2013.01); *A61K 31/341* (2013.01); *A61K 31/351* (2013.01); *A61K 31/355* (2013.01); *A61K 35/60* (2013.01); *A61K 36/06* (2013.01); *A61K 36/88* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,323,648 A | 4/1982 | Tanzawa et al. | |
| 5,604,119 A * | 2/1997 | Haraldsson | C07C 69/003 435/134 |
| 6,046,022 A | 4/2000 | Zhang et al. | |
| 6,410,521 B1 | 6/2002 | Mundy et al. | |
| 6,436,406 B1 | 8/2002 | Yegorova | |
| 6,495,173 B1 | 12/2002 | Yegorova | |
| 6,541,005 B1 | 4/2003 | Yegorova | |
| 6,541,006 B1 | 4/2003 | Yegorova | |
| 6,544,525 B1 | 4/2003 | Yegorova | |
| 6,576,242 B1 | 6/2003 | Yegorova | |
| 10,596,121 B2 | 3/2020 | Opheim et al. | |
| 2003/0157068 A1 | 8/2003 | Liang et al. | |
| 2003/0194394 A1 | 10/2003 | Hong et al. | |
| 2003/0194413 A1 | 10/2003 | Zhang et al. | |
| 2005/0037102 A1 | 2/2005 | Tan et al. | |
| 2006/0003947 A1* | 1/2006 | Udell | A61K 9/4858 514/26 |
| 2006/0034815 A1 | 2/2006 | Guzman et al. | |
| 2006/0052438 A1 | 3/2006 | Ho et al. | |
| 2006/0211763 A1 | 9/2006 | Fawzy et al. | |
| 2006/0241174 A1 | 10/2006 | Mueller et al. | |
| 2007/0141138 A1 | 6/2007 | Feuerstein et al. | |
| 2007/0248621 A1 | 10/2007 | Lowther et al. | |
| 2008/0069927 A1 | 3/2008 | Altemueller | |
| 2008/0102082 A1 | 5/2008 | Senin et al. | |
| 2008/0299187 A1 | 12/2008 | Opheim et al. | |
| 2009/0004290 A1 | 1/2009 | Voelker | |
| 2009/0011012 A1 | 1/2009 | Baum | |
| 2009/0041870 A1 | 2/2009 | Tan et al. | |
| 2009/0182049 A1 | 7/2009 | Opheim | |
| 2010/0119600 A1 | 5/2010 | Opheim | |

(Continued)

FOREIGN PATENT DOCUMENTS

| | | |
|---|---|---|
| CN | 101091708 | 12/2007 |
| CN | 101346138 A | 1/2009 |

(Continued)

OTHER PUBLICATIONS

Abe et al., "Soluble Cell Adhesion Molecules in Hypertriglyceridemia and Potential Significance on Monocyte Adhesion", Artheriosclerosis, Thrombosis, and Vascular Biology, (1988) 18, pp. 723-731.
Bates et al., "Effectiveness of Low-Dose Lovastatin in Lowering Serum Cholesterol", Arch. Intern. Med., (1990) 150, pp. 1947-1950.
Bays, "Statin Safety: An Overview and Assessment of the Data-2005", Am. J. Cardiol., 97(8A), (2006) pp. 6C-26C.
Becker et al., "Simvastatin versus Therapeutic Lifestyle Changes and Supplements: A Randomized Primary Prevention Trial", Meeting Abstract from the 79th Annual Scientific Session of the American Heart Association (Nov. 2006).
Becker et al., "Simvastatin vs Therapeutic Lifestyle Changes and Supplements: Randomized Primary Prevention Trial", Mayo Clin. Proc., (Jul. 2008) 83(7), pp. 758-764.

(Continued)

*Primary Examiner* — Erin M. Bowers
(74) *Attorney, Agent, or Firm* — Foley & Lardner LLP

(57) ABSTRACT

Medicaments and therapeutic compositions comprise Red Yeast Rice extract and omega-3 polyunsaturated fatty acids and/or derivatives thereof, e.g., DHA, derivatives of DHA, EPA, derivatives of EPA or mixtures thereof. One source of the fatty acids or derivatives thereof is fish oil. The compositions are useful for lowering cholesterol and/or triglyceride levels in a subject.

20 Claims, No Drawings

(56) References Cited

U.S. PATENT DOCUMENTS

| | | |
|---|---|---|
| 2012/0171285 A1 | 7/2012 | Opheim |
| 2012/0171311 A1 | 7/2012 | Opheim |
| 2012/0172425 A1 | 7/2012 | Opheim |
| 2012/0195987 A1 | 8/2012 | Opheim |
| 2012/0196928 A1 | 8/2012 | Opheim |
| 2012/0201912 A1 | 8/2012 | Opheim |
| 2012/0219619 A1 | 8/2012 | Opheim et al. |

FOREIGN PATENT DOCUMENTS

| | | |
|---|---|---|
| JP | 2002-027996 | 1/2002 |
| RU | 2342884 | 1/2009 |
| WO | WO-99/29316 | 6/1999 |
| WO | WO-2006/121558 | 11/2006 |
| WO | WO-2007-071733 | 6/2007 |
| WO | WO-2009/027753 | 3/2009 |
| WO | WO-2010/069951 | 6/2010 |

OTHER PUBLICATIONS

Bliznakov et al., "More on the Chinese Red-Yeast-Rice Supplement and its Cholesterol-Lowering Effect", Letters to the Editor and Reply in Am. J. Clin. Nutr., 71 (2000) pp. 152-157.

Durrington et al., "An Omega-3 Polyunsaturated Fatty Acid Concentrate Administered for One Year Decreased Triglycerides in Simvastatin Treated Patients with Coronary Heart Disease and Persisting Hypertriglyceridaemia", Heart (2001) 85, pp. 554-548.

Extended European Search Report dated Jul. 1, 2013 in European application No. 10835095.0.

Fraser, "Effect of Fish Oil and Red Yeast Rice Supplementation on Selected Cardiovascular Disease Risk Factors in Hypercholesterolemic Men", Abstracts of Masters Dissertation, University of Guelph (Canada) in Masters Abstracts International, vol. 40:5, p. 1223 (2002).

Gordon et al., "Marked Variability of Monacolin Levels in Commercial Red Yeast Rice Products", Arch. Intern. Med., (2010) 170(19), pp. 1722-1727.

Herber et al., "An Analysis of Nine Proprietary Chinese Red Yeast Rice Dietary Supplements: Implications of Variability in Chemical Profile and Contents", J. Altern. & Compl. Med., (2001) vol. 7. pp. 133-139.

Herber et al., "Cholesterol-Lowering Effects of a Proprietary Chinese Red-Yeast-Rice Dietary Supplement", Am. J. Clin. Nutri., (1999) 69 pp. 231-236.

International Search Report dated Feb. 11, 2011 in International Application No. PCT/US10/58637.

Jones et al., "Comparative Dose Efficacy Study of Atorvastatin versus Simvastatin, Pravastatin, Lovastatin, and Fluvastatin in Patients with Hypercholesterolemia (The CURVES Study)", Am. J. Cardiol., (1998), 81, pp. 582-587.

Li et al., "Identification and Chemical Profiling of Monacolins in Red Yeast Rice Using High-Performance Liquid Chromatography with Photodiode Array Detector and Mass Spectrometry", J. Pharm. & Biomed. Analy., 35 (2004), pp. 1101-1112.

Li et al., "Monascus purpureus-Fermented Rice (Red Yeast Rice): A natural Food Product that Lowers Blood Cholesterol in Animal Models of H7percholesterolemia", Nutrition Research, 18(1) (1998), pp. 71-81.

Lin et al., "Efficacy and Safety of Monascus purpureus Went Rice in Subjects with Hyperlipidemia", European Journal of Endocrinology, vol. 153. pp. 679-686 (2005).

Liu et al., "Accelerated Solvent Extraction of Monacolin K from Red Yeast Rice and Purification by High-Speed Counter-Current Chromatography", J. Chromatography B (2010), 878, pp. 2881-2885.

Ma et al., "Constituents of Red Yeast Rice, a Traditional Chinese Food and Medicine", J. Agric. Food Chem. (2000) vol. 48, pp. 5220-5225.

Monograph on "Monascus Purpureus (Red Yeast Rice)", Alternative Medicine Review (2004) 9(2) pp. 208-210.

Office Action dated Jan. 14, 2013 in U.S. Appl. No. 13/443,736 (US 2012-0196928).

Office Action dated Feb. 3, 2016 in U.S. Appl. No. 12/630,686 (US 2010-0119600).

Office Action dated Feb. 27, 2015 in U.S. Appl. No. 13/443,736 (US 2012-0196928).

Office Action dated Apr. 8, 2013 in U.S. Appl. No. 13/420,403 (US 2012-0171311).

Office Action dated Apr. 8, 2013 in U.S. Appl. No. 13/420,410 (US 2012/0171285).

Office Action dated Apr. 9, 2013 in U.S. Appl. No. 13/420,406 (US 2012-0172425).

Office Action dated Apr. 29, 2015 in U.S. Appl. No. 12/630,686 (US 2010-0119600).

Office Action dated Jun. 3, 2011 in U.S. Appl. No. 11/757,340 (US 2008-0299187).

Office Action dated Jun. 16, 2010 in U.S. Appl. No. 11/757,340 (US 2008-0299187).

Office Action dated Jul. 1, 2013 in U.S. Appl. No. 12/630,686 (US 2010-0119600).

Office Action dated Jul. 9, 2012 in U.S. Appl. No. 13/443,736 (US 2012-0196928).

Office Action dated Sep. 26, 2013 in U.S. Appl. No. 13/443,735 (US 2012-0195987).

Office Action dated Oct. 11, 2012 in U.S. Appl. No. 12/630,686 (US 2010-0119600).

Office Action dated Oct. 11, 2012 in U.S. Appl. No. 13/443,735 (US 2012-0195987).

Office Action dated Oct. 12, 2012 in U.S. Appl. No. 13/443,739 (US 2012-0201912).

Office Action dated Oct. 17, 2014 in U.S. Appl. No. 13/457,907 (US 2012-0219619).

Office Action dated Oct. 24, 2013 in U.S. Appl. No. 13/443,739 (US 2012-0201912).

Office Action dated Dec. 19, 2016 in U.S. Appl. No. 12/630,686 (US 2010-0119600).

Office Action dated Dec. 24, 2013 in U.S. Appl. No. 13/457,907 (US 2012-0219619).

Ong et al., "Statin Alternatives or Just Placebo: An Objective Review of Omega-3, Red Yeast Rice and Garlic in Cardiovascular Therapeutics", Chin Med J. (2008) 121(16), pp. 1588-1594.

Ridker et al., "Effects of n-3 Fatty Acid Therapy on Lipids and sCAMs", Lipids Online, (Oct. 2001), http://216.27.67.143/slides/slide01.cfm7q=omacor&dpg=1.

Thompson et al., "Statin-Associated Myopathy", JAMA, 289(13), (2003), pp. 1681-1690.

Venero et la., "Lipid-Lowering Efficacy of Red Yeast Rice in a Population Intolerant of Statins", Am. J. Cardiol (2010) vol. 105, pp. 664-666.

Wang et al., "Multicenter Clinical Trial of the Serum Lipid-Lowering Effects of a Monascus Purpureus (Red Yeast) Rice Preparation from Traditional Chinese Medicine", Current Therapeutic Research, (1997) Vo. 58:12, pp. 964-078.

Website, "Monacolin K—Monacolin K Manufacturers, Suppliers and Exporters on Alibaba.com", (as of Apr. 9, 2012), available at http://www.alibaba.com/trade/search?IndexArea=product_en&SearchText=monacolin K, (attached is a print-out of the first 50 listings of the 1,071 manufacturers, suppliers, and exporters that are shown on that website.

Written Opinion of the International Searching Authority dated Feb. 11, 2011 in International Application No. PCT/US10/58637.

Chung et al., "The Impact of Exercise on Statin-Associated Skeletal Muscle Myopathy," PLoS One 11(12): e0168065 (2016).

Dyerberg et al., "Bioavailability of marine n-3 fatty acid formulations," Prostaglandins, Leukotrienes and Essential Fatty Acids 83 (2010) 137-141.

Fan et al., "Screening and Management of Lipids," Guidelines for Clinical Care (Ambulatory), in UMHS Lipid Therapy Guideline (2014) University of Michigan: Ann Arbor, MI, pp. 1-20.

Holme et al., "Lipoprotein predictors of cardiovascular events in statin-treated patients with coronary heart disease. Insights from the

(56) References Cited

OTHER PUBLICATIONS

Incremental Decrease in End-Points Through Aggressive Lipid-lowering Trial (IDEAL)," Annals of Medicine, 40(6): 456-464 (2008).

Laidlaw et al., "A randomized clinical trial to determine the efficacy of manufacturers' recommended doses of omega-3 fatty acids from different sources in facilitating cardiovascular disease risk reduction," Lipids in Health and Disease (2014) 13:99, 13 pages, Available online, URL: http://www.lipidworld.com/content/13/1/99.

* cited by examiner

SUBSTANCES FOR REDUCING OCCURRENCE OF MAJOR CARDIAC EVENTS COMPRISING RED YEAST RICE EXTRACT AND OMEGA-3 POLYUNSATURATED FATTY ACID OR DERIVATIVE THEREOF

CROSS-REFERENCE TO RELATED APPLICATION

This application is a continuation of U.S. patent application Ser. No. 15/870,138, filed Jan. 12, 2018, which is a continuation of U.S. patent application Ser. No. 12/630,686, filed Dec. 3, 2009, which is a continuation-in-part of U.S. patent application Ser. No. 11/757,340 filed Jun. 1, 2007, the entire contents of which are incorporated herein by reference. All publications, patents, patent applications, databases and other references cited in this application, all related applications referenced herein, and all references cited therein are incorporated herein by reference in their entirety as if restated here in full and as if each individual publication, patent, patent application, database or other reference were specifically and individually indicated to be incorporated by reference.

BACKGROUND OF THE INVENTION

Field of the Invention

The invention relates to compositions and the use of such compositions in nutritional supplements and medicaments, wherein the compositions are combinations of Red Yeast Rice extract, having hydroxymethylglutaryl-CoA (HMG-CoA) reductase inhibitor activity, with omega-3 polyunsaturated fatty acid or derivatives thereof derived from fish oils or other sources of omega-3 polyunsaturated fatty acids or derivatives thereof.

Description of the Prior Art

Statins (which are members of a group of HMG-CoA reductase inhibitors) are a group of hypolipidemic agents, used as pharmaceutical agents to lower cholesterol levels in people with or at risk for cardiovascular disease. Statins lower cholesterol by inhibiting the enzyme HMG-CoA reductase, which is the rate-limiting enzyme of the mevalonate pathway of cholesterol synthesis. Inhibition of this enzyme in the liver stimulates low-density lipoprotein (LDL) receptors, resulting in an increased clearance of LDL, so-called "bad cholesterol," from the bloodstream and a decrease in blood cholesterol levels.

Statins are potent cholesterol-lowering agents, and have been reported to lower LDL cholesterol by 30-50% (see Jones, P., Kafonek, S., Laurora, I., et al., "Comparative dose efficacy study of atorvastatin versus simvastatin, pravastatin, lovastatin, and fluvastatin in patients with hypercholesterolemia (the CURVES study)," *Am J Cardiol* 1998; 81-(5); 582-7). Statins are classified as either synthetic or fermentation derived. Lovastatin was isolated from a strain of *Aspergillus terreus* and it was the first statin approved by the FDA as a drug (August 1987). Lovastatin is a water insoluble, white crystalline solid. The aqueous insolubility of lovastatin leads to inadequate dissolution in gastrointestinal fluids and, hence, poor absorption, distribution, and targeted organ delivery. Solubility of lovastatin is enhanced by reaction with 3-cyclodextrin, an oligosaccharide which improves the solubility of lovastatin. The improvement of aqueous solubility in such a case is a valuable goal to improve therapeutic efficacy. Lovastatin can also produce slight to moderate increases in high density lipoproteins (HDL) (10-20%), and slight decreases in triglycerides (5-10%). The usual daily dose of lovastatin is 20-80 mg/day. The statin drugs include lovastatin, pravastatin, fluvastatin, atorvastatin, simvastatin, rosuvastatin, and cerivastatin.

Compounds similar to lovastatin have also been found in a natural fermentation product known as Red Yeast Rice. These compounds are also HMGCoA reductase inhibitors. A monograph published in Alternative Medicine Review (Volume 9, Number 2, 2004) reports that the HMG-CoA reductase inhibitor activity in Red Yeast Rice comes from a naturally occurring family of nine compounds called "monacolins," each of which has HMG-CoA reductase inhibitor activity. Additional active ingredients in Red Yeast Rice include sterols (beta-sitosterol, campesterol, sigmasterol, and sapogenin), isoflavones, and monounsaturated fatty acids (see Heber D, et al., Cholesterol lowering effects of proprietary Chinese red yeast rice dietary supplement, *Am J Clin Nutr* 1999:69:231-236). One of the monacolins in Red Yeast Rice, monacolin K, is said to be the lactone form of the statin drug lovastatin, which is converted to the active acid form in vivo by the liver.

Red Yeast Rice is a common foodstuff in Asian countries where the average daily intake is 14-55 grams. The nutritional supplement derived from Red Yeast Rice is known as Red Yeast Rice extract. It is obtained by drying the fermented product of rice on which the yeast *Monascus pupureus* has been grown and extracting the dried product with a solvent, usually aqueous ethanol or water. The Red Yeast Rice extract thus produced typically contains about 0.2 wt. % monacolin K and about 0.5 wt. % total monacolins.

U.S. Pat. No. 6,046,022, issued Apr. 4, 2000 to Zhang, et al (Peking University), discloses some methods of making high lovastatin (monacolin K) Red Yeast Rice and using Red Yeast Rice and Red Yeast Rice extract. U.S. Pat. No. 6,046,022 is hereby incorporated by reference herein in its entirety.

U.S. Pat. Nos. 6,541,005; 6,436,406; 6,495,173; 6,544,525; 6,576,242; and 6,541,006, issued Apr. 1, 2003; Aug. 20, 2002; Dec. 17, 2002; Apr. 8, 2003; Jun. 10, 2003; Apr. 1, 2003; and Jun. 25, 2002, respectively to Yegorova and U.S. Pat. No. 6,410,521, issued Jun. 25, 2002 to Mundy et al., disclose methods of using Red Yeast Rice. All of these patents are incorporated herein by reference in their entirety.

U.S. Patent Application Publication No. 20060211763, published Sep. 21, 2006 by Fawzy et al., discloses a statin drug dissolved in a solvent system comprising natural or synthetic omega-3 fatty acids and U.S. Patent Application Publication No. 20060034815, published Feb. 16, 2006 by Guzman et al., discloses omega-3 oil solutions of one or more statins.

Omega-3 polyunsaturated fatty acids and derivatives thereof can be derived from fish oils and are known to reduce serum triglycerides (see Abe Y, El-Masri B, et al, Soluble cell adhesion molecules in hypertriglyceridemia and potential significance on monocyte adhesion. *Arteriosler Thromb Vasc Biology* 1998:18:723-731) and adverse coronary events. The principal active ingredients in fish oil are 5,8,11,14,17-eicosapentaenoic acid (eicosapentaenoic acid (EPA), 20:5 (n–3)) and 4,7,10,13,16,19-docosahexaenoic acid (docosahexaenoic acid (DHA), 22:6 (n–3)). EPA and DHA have been given at a combined dose of 4 g/day for seven months to hypertriglyceridemic patients resulting in a reduction of 47% in triglycerides (see Ridker, Paul, Effects of n-3 Fatty Acid Therapy on Lipids and sCAMs—hiflammatory Markers, Pharmacotherapy and Clinical Trials, Lipids Online.org, posted: Oct. 3, 2001, reviewed Oct. 4, 2001).

The effects of statin drugs and omega-3 polyunsaturated fatty acids or derivatives thereof have been reported to be cumulative. When 59 patients who were already receiving 10-40 mg daily of the statin simvastatin were given 2 grams twice daily of EPA+DHA, there was a further sustained significant decrease of 20-30% in triglycerides (see Durington P, Bhatnager, et al, An omega-3 polyunsaturated fatty acid concentration administered for one year decreased triglycerides in simvastin treated patients with *CM. Heart* 2001:85(5) 544-548).

Omega-3 polyunsaturated fatty acids and derivatives thereof are also well known to those skilled in the art to reduce inflammation, decrease arrhythmias, decrease risk of sudden cardiac death and cardiac arrest.

SUMMARY OF THE INVENTION

Further provided in accordance with the present invention is a therapeutic composition comprising (1) at least one omega-3 polyunsaturated fatty acid, at least one pharmaceutically acceptable omega-3 polyunsaturated fatty acid derivative or mixtures thereof, and (2) Red Yeast Rice extract.

The present invention further provides such a therapeutic composition wherein component (1) comprises EPA, derivatives of EPA, DHA, derivatives of DHA or mixtures thereof. The therapeutic compositions may be compositions wherein the derivatives of EPA and derivatives of DHA are glycerides. Further provided are compositions wherein component (1) is a mixture comprising about 35 wt. % triglycerides of EPA and about 25 wt. % triglycerides of DHA.

The present invention further provides a therapeutic composition wherein component (1) is a mixture comprising at least about 60 wt. % of a combination of EPA and DHA in a weight ratio of EPA:DHA of from about 1.4:1 to about 5:1, wherein the combination is at least about 60% in the triglyceride form of the EPA and DHA and the balance is at least about 80% mono- and di-glycerides. Also provided are compositions wherein the combination comprises about 65 wt. % triglycerides of EPA and about 15 wt. % triglycerides of DHA or wherein the combination comprises about 75 wt. % triglycerides of EPA and about 15 wt. % triglycerides of DHA. Also provided are compositions wherein the combination is at least about 80% in the triglyceride form, at least about 90% in the triglyceride form, at least about 98% in the triglyceride form, or least about 98% in the triglyceride form and the remainder is monoglycerides, diglycerides or both. The present invention further provides therapeutic compositions wherein the combination comprises about 65 wt. % triglycerides of EPA and about 15 wt. % triglycerides of DHA.

In accordance with the present invention there is further provided compositions wherein the Red Yeast Rice extract comprises at least about 0.1 wt. % monacolin K, wherein Red Yeast Rice extract comprises at least about 0.2 wt. % monacolin K and at least about 0.4 wt. % total monacolins, and wherein the Red Yeast Rice extract comprises at least about 0.4 wt. % monacolin K.

The present invention also provides a dose of the medicament or therapeutic composition wherein the dose of medicament or therapeutic composition comprises about 1000 mg of EPA and/or derivatives of EPA plus DHA and/or derivatives of DHA and about 1200 mg of Red Yeast Rice extract, wherein the dose comprises about 2000 mg of EPA and/or derivatives of EPA plus DHA and/or derivatives of DHA and about 2400 mg of Red Yeast Rice extract, or wherein the dose comprises about 4000 mg of EPA and/or derivatives of EPA plus DHA and/or derivatives of DHA and about 2400 mg of Red Yeast Rice extract.

In accordance with the present invention there is further provided a method of reducing serum cholesterol, triglycerides or both in a subject comprising administering the subject a dosage comprising the above-recited therapeutic compositions.

DETAILED DESCRIPTION OF EMBODIMENTS

The present invention relates to a medicament comprising Red Yeast Rice extract dispersed in fish oil. In some embodiments, the medicament includes compositions in which the fish oil comprises at least about 60% of omega-3 oils, or at least about 70% omega-3 oils. In some embodiments, the medicament includes compositions in which the omega-3 oils comprise about 50% EPA and about 35% DHA, or in which the omega-3 oils comprise about 69% EPA and about 16% DHA. In some embodiments, the medicament includes compositions in which the Red Yeast Rice extract comprises at least about 0.1 wt. % monacolin K. In some embodiments, the medicament includes compositions in which the Red Yeast Rice extract comprises at least about 0.2 wt. % monacolin K and at least about 0.4 wt. % total monacolins. In some embodiments, the weight ratio of fish oil to Red Yeast Rice extract is in the range between 1.4 and 2.8. In some embodiments, the medicament further comprises a dispersing agent. In some embodiments, the dispersing agent comprises 3% lysine and 2% bamboo. In some embodiments, the medicament further comprises a soft gelatin capsule into which the fish oil, Red Yeast Rice extract and dispersing agent are loaded. In some embodiments, the medicament comprises a daily dose of the medicament which is delivered by an integral number of capsules. In some embodiments, the daily dose of medicament comprises about 1000 mg of EPA and/or derivative of EPA plus DHA and/or derivative of DHA and about 1200 mg of Red Yeast Rice extract, or the daily dose of medicament comprises about 2000 mg of EPA and/or derivative of EPA plus DHA and/or derivative of DHA and about 1200 mg of Red Yeast Rice extract, or the daily dose of medicament comprises about 2000 mg of EPA and/or derivative of EPA plus DHA and/or derivative of DHA and about 2400 mg of Red Yeast Rice extract, or the daily dose of medicament comprises about 4000 mg of EPA and/or derivative of EPA plus DHA and/or derivative of DHA and about 2400 mg of Red Yeast Rice extract. In some embodiments, the medicament further comprises an antioxidant. In some embodiments, the antioxidant is chosen from the group consisting of rosemary, vitamin E, astaxanthine, carnitine, ascorbyl palmitate, and tocopherols.

The present invention further relates to a method of reducing serum cholesterol, triglycerides or both in a subject comprising administering a daily dosage comprising EPA and/or derivative of EPA, DHA and/or derivative of DHA, and Red Yeast Rice extract. In some embodiments, the daily dosage comprises about 4000 mg of EPA and/or derivative of EPA plus DHA and/or derivative of DHA and about 2400 mg of Red Yeast Rice extract, or the daily dosage comprises about 1000 mg of EPA and/or derivative of EPA plus DHA and/or derivative of DHA and about 1200 mg of Red Yeast Rice extract, or the daily dosage comprises about 2000 mg of EPA and/or derivative of EPA plus DHA and/or derivative of DHA and about 1200 mg of Red Yeast Rice extract, or the daily dosage comprises about 2000 mg of EPA and/or derivative of EPA plus DHA and/or derivative of DHA and about 2400 mg of Red Yeast Rice extract.

The invention also relates to compositions comprising Red Yeast Rice extract dispersed in omega-3 polyunsaturated fatty acids or derivatives thereof, and the use of such compositions to treat a subject. The Red Yeast Rice extract preferably comprises at least one and preferably more than one monacolin compound. In some embodiments, the monacolin compound comprises monacolin K. In some embodiments, the monacolin compounds comprise monacolin K and at least one other monacolin compound. In some embodiments, the monacolin compounds comprise all of the monacolin compounds in Red Yeast Rice. In some embodiments, the Red Yeast Rice extract contains about 0.2 wt. % monacolin K and about 0.5 wt. % of total monacolins.

The compositions of the present provide several advantages over the use of lovastatin to reduce cholesterol and triglyceride level in a subject. For instance, the Red Yeast Rice extract is water soluble, whereas lovastatin is not. As noted above, the water insolubility of lovastatin leads to inadequate dissolution in gastrointestinal fluids and, hence, poor absorption, distribution, and targeted organ delivery. While the water solubility of lovastatin can be enhanced, it is believed that the water soluble Red Yeast Rice extract will enter the subjects system easier than lovastatin.

It is also emphasized that Red Yeast Rice extract can produce better lipid reducing results at lower dosages (based on the amount of monacolin in the Red Yeast Rice extract) than lovastatin. This reduces the risk of undesirable and possibly harmful side effects in the subject.

The Red Yeast Rice extract is prepared by fermenting white rice, preferably non-glutinous white rice, with *Monascus purpureus* strain of yeast by culturing said *Monascus purpureus* strain in a culture medium comprising rice at a temperature of about 15° C. to about 35° C. for a period of about 2 to about 20 days to provide a crude fermentation product containing Red Yeast Rice; drying said crude fermentation product to obtain Red Yeast Rice, extracting said Red Yeast Rice with a solvent to provide an extract; and drying said extract to remove the solvent and produce Red Yeast Rice extract. The solvent is preferably either aqueous ethanol or water. Other culture media may also be added to the rice. For example, sugar; an additional carbon source chosen from the group consisting of glycerine, malt, and potato juice; and thick beet juice or mixtures thereof may be used. In addition, a defoamer may be added.

In some embodiments, the Red Yeast Rice extract used in the compositions of the present invention contains at least about 0.1 wt. % monacolin K. In some embodiments, the Red Yeast Rice extract contains at least about 0.15 wt. %, at least about 0.2 wt. %, at least about 0.25 wt. %, at least about 0.3 wt. %, at least about 0.35 wt. % or at least about 0.4 wt. % monacolin K. In some embodiments, the Red Yeast Rice extract contains at least about 0.4 wt. %, at least about 0.45 wt. % or at least about 0.5 wt. % of total monacolins. In some embodiments, the Red Yeast Rice extract used in the compositions of the present invention contains at least about 0.4 wt. % monacolin K.

Red Yeast Rice extracts are readily available in commerce in the United States and may be purchased already prepared. Preferred typical daily dose of Red Yeast Rice extract is about 1.2 to about 2.4 grams per day, which were the dosages used in human clinical trials.

Omega-3 Polyunsaturated Fatty Acids

As used herein, the term "omega-3 polyunsaturated fatty acid(s)" refers to a family of unsaturated fatty carboxylic acids that have in common a carbon-carbon bond in the n−3 position (i.e., the third bond from the methyl end of the molecule). Typically, they contain from about 16 to about 24 carbon atoms and from three to six carbon-carbon double bonds. Omega-3 polyunsaturated fatty acids can be found in nature, and these natural omega-3 polyunsaturated fatty acids frequently have all of their carbon-carbon double bonds in the cis-configuration.

Examples of omega-3 polyunsaturated fatty acids include, but are not limited to, 7,10,13-hexadecatrienoic acid (sometimes abbreviated as 16:3 (n−3)); 9,12,15-octadecatetrienoic acid (α-linolenic acid (ALA), 18:3 (n−3)); 6,9,12,15-octadecatetraenoic acid (stearidonic acid (STD), 18:4 (n−3)); 11,14,17-eicosatrienoic acid (eicosatrienoic acid (ETE), 20:3 (n−3)); 8,11,14,17-eicosatetraenoic acid (eicosatetraenoic acid (ETA), 20:4 (n−3)); 5,8,11,14,17-eicosapentaenoic acid (eicosapentaenoic acid (EPA), (20:5 (n−3)); 7,10,13,16,19-docosapentaenoic acid (docosapentaenoic acid (DPA), 22:5 (n−3)); 4,7,10,13,16,19-docosahexaenoic acid (docosahexaenoic acid (DHA), 22:6 (n−3)); 9,12,15,18,21-tetracosapentaenoic acid (tetracosapentaenoic acid, 24:5 (n−3)); and 6,9,12,15,18,21-tetracosahexaenoic acid (tetracosahexaenoic acid, 24:6 (n−3)).

Eicosapentaenoic acid (EPA) and docosahexaenoic acid (DHA) are found in nature in fish oils, and have been used in a variety of dietary/therapeutic compositions. EPA and DHA are preferred omega-3 polyunsaturated fatty acids in the present invention.

Omega-3 Polyunsaturated Fatty Acid Derivatives

As used herein, the term "omega-3 polyunsaturated fatty acid derivative(s)" refers to omega-3 polyunsaturated fatty acids that have been reacted with another compound or otherwise modified so that the omega-3 polyunsaturated fatty acid no longer contains a free carboxylic acid. Examples of omega-3 polyunsaturated fatty acid derivatives include salts, esters (such as alkyl esters including, but not limited to, methyl and ethyl esters) and glycerides of omega-3 polyunsaturated fatty acids. The omega-3 polyunsaturated fatty acid can also be one or more of the fatty acid moieties in a phospholipid molecule.

As used herein, the term "glyceride" means a glycerol molecule (i.e., $OHCH_2CHOHCH_2OH$) in which one, two or all three of the hydroxyls have been esterified with a carboxylic acid, e.g., an omega-3 polyunsaturated fatty acid. Thus, "triglyceride" refers to glycerides in which all three hydroxyls on the glycerol have been esterified with (the same or different) carboxylic acids. "Diglyceride" refers to glycerides in which only two of the hydroxyls on the glycerol have been esterified with (the same or different) carboxylic acids. "Monoglyceride" refers to glycerides in which only one hydroxyl on the glycerol has been esterified with a carboxylic acid.

Omega-3 fatty acids are found in nature in the triglyceride form (a glycerol with three fatty acids attached). The natural triglyceride form as found in raw fish oil cannot be readily separated as it occurs into purified EPA/DHA mixtures by ordinary means such as distillation or crystallization, because the fatty acids are non-uniformly distributed among the triglyceride molecules. There are very few, if any, single triglyceride molecules which are composed of either three EPAs or three DHAs. Typically, there is a DHA, an EPA, and another fatty acid in a triglyceride molecule. So in order to purify fatty acids to increase the proportion of EPA, DHA, or the total fraction of omega-3's, it is necessary to hydrolyze the triglycerides to remove at least some fatty acids from the glycerol.

The triglycerides may be converted by any method known to one skilled in the art without limitation. For example, the triglycerides may be converted by lipase-catalyzed esterification or lipase catalyzed acidolysis with ethyl or lauryl alcohol, which can selectively leave the highest amount of EPA and DHA bonded to glycerols and remove other components, leaving EPA and/or DHA as mono- or di-glycerides. The mono- and di-glycerides can then be separated into fractions with different EPA/DHA ratios, by methods familiar to those skilled in the art such as multiple stage vacuum distillation and/or fractional crystallization in urea. Advantageously, the purified EPA and DHA esters, after concentration, can be reattached to glycerol molecules using enzymatic reacylation to recreate glycerides which are otherwise identical to the original natural triglycerides, except that they are more concentrated in EPA and DHA combined, and they may also have a different ratio of EPA:DHA than the original fish oil. In some embodiments, at least 60% of the omega-3 fatty acids, and preferably 70% or more are converted to the triglyceride form in the reacylation process. The process may be successively repeated with addition of additional catalyst and/or enzyme and additional EPA and DHA until the desired specification proportions are met. About 60% of triglycerides can be made in the first pass of reacylation, with most of the remainder of the product being mono- and di-glycerides.

Polyunsaturated fatty acid triglycerides can be prepared using the following method:

1. Removal of Free Fatty Acids

Raw fish oil in the natural triglyceride molecular form preferably from anchovies and sardines which contain about 18% EPA and 12% DHA is heated to 60° C. to decrease viscosity. Sodium oxide is added to bind with free fatty acids in the oil. The mixture is moved to a separator where sodium oxide bound to free fatty acids (soap) floats to the top and is removed.

The oil is then moved to a second separator where warm water is preferably added to help remove traces of sodium oxide, as sodium oxide partitions to water, yet does not interact with the fish oil.

Citric acid may then be added to support splitting the oil from the combination of water and sodium oxide. The oil is then cooled to 30° C. to protect it from oxidation.

2. Stripping and Purification

Oil is moved to a separate stripping tank, and heated to 200° C. Ethyl esters can be added to support the removal of impurities, which bind to ethyl esters. Impurities such as dioxins, heavy metals, pcbs, fire retardants, furans and others evaporate and are drawn to the middle of the tank where a refrigerating element cools them down and drain them. The added esters are also removed with the impurities.

3. Esterification

The oil is moved to an esterification tank. Ethanol and sodium metal are added. Sodium metal is a catalyst for breaking off fatty acid strands from the glycerol backbone of the triglyceride fatty acid molecule, the free fatty acids then combined with ethanol to form ethyl esters. Water can be added to bind to sodium metal, where the combination of water and sodium metal can be removed.

4. Molecular Distillation

The oil is then moved to a distiller where it is heated to about 120° C. under vacuum. Mono esters and shorter carbon chain molecules move to the middle where they are cooled and drained, leaving longer carbon chains remaining as a concentrate. The process typically increases the key fatty acids by 100% during the first distillation; typically between 30-50% during the second distillation. The process can be repeated, although preferably the process is ideally only repeated once, as when oils undergo heat it can produce oxidation and degradation of the fatty acids in general. Oil waste is also increasing with repeated distillation, making the process less economical.

5. Reesterification (Reacylation)

The oil is then moved to a reesterification tank where the ethyl ester molecules are reconverted to the triglyceride form, which is the natural form of that fatty acid molecule. 98% of fats ingested by humans are in this natural triglyceride form.

The esterification process takes place under low vacuum at about 80° C. Glycerol is added to form the backbone of the glyceride molecules. Nitrogen can be added from the bottom of the tank to cause oil movement. Lipase enzymes are added as catalysts to facilitate the fatty acids binding to glycerol. The vacuum in the distillation tank removes the ethanol which was previously bound to the fatty acids. The enzymes used are lipases produced from bacteria or yeast. Perhaps the most effective enzymes are *Candidan antarctica* lipase, and Chromobacterium *Viscosum* Lipase; other enzymes that can be used effectively are *Psuedomonas, Mucor miehei*, and *Candida Cylindracea* as well as other enzymes may also be used.

The reesterification process typically takes 24 hours, at which point the triglycerides typically reaches 60-65%, the remaining glycerides being diglycerides and monoglycerides. Around 3% of the fish oil will remain as ethyl esters, which can be removed together with the ethanol. Adding additional enzymes and/or continuing the enzymatic process can produce triglyceride molecule concentration of up to 99%. The 60-65% level is probably optimum from an economic point of view.

6. Winterization

The oil in triglyceride form is then moved to a cooling tank at 0° C., where saturated fats, in particular stearic acid are crystallized. The pulp is then pumped to a filter press, where the crystals are removed, essentially removing the vast majority of saturated fats from the oil. Depending on the amount of saturated fats in the oil, approximately 5-10% of the oil is lost during this process.

7. Bleaching

The oil is then removed to a bleaching tank at 60° C., where bleaching earth or bentonite earth is added to the oil. Any water in the oil evaporates due to the temperature. Any remaining impurities (trace minerals, etc) in the oil attach to the bentonite earth. The oil is then run through a bentonite earth filter to remove the bentonite earth together with the impurities.

8. Deodorization

Although not a necessary step, it is advantageous to move the oil to a deodorization tank. The tank contains low vacuum at 120° C. Steam is added at the bottom of the tank, which connects to color and odor molecules (oxidated matter, peroxides) which again travel into the vacuum system and into a residue container. This process gives the oil a neutral color with virtually zero taste and odor.

9. Mixing

The oil is then moved to a separate storage tank. Depending on the concentration of EPA and DHA desired, various batches can be mixed to yield the concentration desired for the final product.

10. Addition of Antioxidant

Antioxidants, in particular rosemary and mixed tocopherols can be added to the final oil to dramatically reduce the oxidation process.

11. Drumming

The oil is then drummed in stainless steel drums for storage and topped off with nitrogen to remove oxygen and minimize the potential for oxidation.

As used herein, the term "pharmaceutically acceptable" means that the material to which it refers is not harmful to the subject.

In some embodiments, the composition of the invention employs a mixture of omega-3 polyunsaturated fatty acids and/or derivatives that contain glycerides. For example, in one embodiment, the mixture contains about 35 wt. % triglycerides of EPA and about 25 wt. % triglycerides of DHA and about 10% other omega-3 fatty acids or derivatives thereof. In some embodiments, the mixture contains about 65 wt. % triglycerides of EPA, about 15 wt. % triglycerides of DHA and about 20% other omega-3 fatty acids or derivatives thereof, wherein the EPA and DHA are at least about 60% in the triglyceride form and the balance are at least about 90% of mono- and di-glycerides. In some embodiments, the mixture contains about 75% EPA and about 15% DHA, wherein at least about 60% of the combination of DHA and EPA are in the triglyceride form and the balance is at least about 90% mono- and di-glycerides. In another embodiment, the mixture can contain at least about 60 wt. % of a combination of EPA and DHA in a weight ratio of EPA:DHA of from about 1.4:1 to about 5:1 (for example, 2:1 to 5:1, 3:1, 4:1 or 4.3:1) wherein the combination is at least about 60% (e.g., at least about 80% or at least about 90% or at least about 98%) in the triglyceride form of the fatty acids and the balance is at least about 80% mono- and di-glycerides. In some embodiments, the combination is at least about 98% in the triglyceride form, with the balance being in the monoglyceride and/or diglyceride forms. Some of the above compositions are disclosed in copending U.S. patent application Ser. No. 12/015,488, filed Jan. 16, 2008 by Opheim. That patent application is incorporated by reference herein in its entirety.

Sources of the omega-3 polyunsaturated fatty acids or derivatives thereof include natural sources including, but not limited to, fish oil (e.g., cod liver oil), flax seed oil, marine oils, sea oils, krill oil, algae and the like. Fish oil is a preferred source.

It is preferred to use a high quality source of omega-3 polyunsaturated fatty acids or derivatives thereof which is rich in omega-3 oils, preferably containing at least 70% omega-3 oils. The oil can also be rich in EPA and DHA. Preferably, at least 75% of the omega oils are EPA+DHA, and more preferably 85% or more are EPA-+DHA. The daily dose of omega-3 oils is about 1 to about 4 grams of omega-3 oil. One possible source is a balanced omega-3 formula such as Nordic Naturals, Inc.'s ProOmega nutritional supplement, which is 70% omega-3 oils of which 50.8% is EPA, 35.1% is DHA and 14.1% is other omega-3 polyunsaturated fatty acids or derivatives thereof.

One preferred source of omega-3 polyunsaturated fatty acids or derivatives thereof is Pro-EPA nutritional supplement sold by Nordic Naturals, Inc. It comprises 69.1% EPA, 16.3% DHA, and 14.6% other omega-3 polyunsaturated fatty acids or derivatives thereof. Still another preferred source of omega-3 polyunsaturated fatty acids or derivatives thereof is Nordic Naturals, Inc.'s Pro-EFA Xtra which comprises 56.9% EPA, 14.7% DHA, 17.2% GLA (omega-6 gamma-linolenic acid, i.e., 6,9,12-octadecatrienoic acid (18:3 (n–6) or derivative thereof)), and 11.2% other omega-3 polyunsaturated fatty acids or derivatives thereof. The Pro-EFA Xtra formula adds an omega-6 polyunsaturated fatty acid or derivatives thereof, GLA, and makes a powerful anti-inflammatory mixture.

The Red Yeast Rice extract is water soluble and is not soluble in the omega-3 oil. In some embodiments, a dispersant is used to keep the Red Yeast Rice extract in suspension. In some embodiments, the dispersant is about 70% silica bamboo with lysine made from sunflower oil. A suitable method for making a mixture of the present invention is to vigorously mix 24 weights of Red Yeast Rice extract with 36 weights of fish oil (containing a suitable amount of omega-3 polyunsaturated fatty acids or derivatives thereof), 1.2 weights of bamboo (2%), and 1.8 weights of lysine (3%). The resulting mixture may then be diluted to the desired omega-3 oil to Red Yeast Rice extract ratio. In some embodiments, the omega-3/Red Yeast Rice extract is then encapsulated in soft gelatin capsules for dispensing. The capsules are typically of such a size that an integral number of capsules comprise a daily dosage of the mixture.

In some embodiments, a dosage of the omega-3/Red Yeast Rice mixture further includes antioxidants such as rosemary, vitamin E, astaxanthine, carnitine, ascorbyl palmitate, tocopherols or other antioxidants known in the art for stabilizing fish oil and/or omega-3 polyunsaturated fatty acids or derivatives thereof.

Comparison Between Red Yeast Rice Extract and Lovastatin

Red Yeast Rice extract contains monacolin K, the lactone form of the statin drug Mevacort (lovastatin). Red Yeast Rice extract has been tested in clinical trials at daily dosages of 1.2 g and 2.4 g. The monacolin K content of the Red Yeast Rice extract used in the clinical trials was 0.20% of the Red Yeast Rice extract. The monacolin K dose was therefore 2.4 to 4.8 mg/day. At 2.4 mg/day of monacolin K, the total cholesterol, LDL cholesterol, and triglycerides dropped by 23%, 31%, and 34% respectively. At 4.8 mg/day, the reduction was 17%, 23%, and 16% respectively (see Monograph by Thorne Research Inc., Alternative Medicine Review. Volume 9, Number 1 2004).

Lovastatin has been shown to have a cholesterol lowering effect in doses ranging from 5 to 80 mg/day (see Bates, M, et al, Effectiveness of low dosage lovastatin in lowering serum cholesterol. Experience with 56 patients. *Archives of Internal Medicine* 1990:150: 1947-1950). A study was performed to show the effectiveness of low-dose lovastatin in lowering serum cholesterol (see Heber D, et al., Cholesterol lowering effects of proprietary Chinese red yeast rice dietary supplement, *Ann J Clin Vutr* 1999, 69:231-236). Fifty-six patients were given 20 mg/day of lovastatin for 24 weeks. Total cholesterol fell by 26% and triglycerides fell by 12%.

Mevacor® (lovastatin) in its package insert reported extensive clinical trials at dosages of 10, 20, and 40 mg/day. Total cholesterol was reduced in the range from 16-24%, LDL was reduced by 21-32%, and triglycerides were reduced by 10 to 6% (higher reduction observed at lower dosage).

It should be noted that Red Yeast Rice extract at a dosage of 2.4 mg/day of monacolin K produced better lipid reducing results than Mevacor at 10-40 mg/day. It is, therefore, unlikely that the lipid lowering effects with Red Yeast Rice result from the monacolin K content alone of Red Yeast Rice, but are probably attributable in whole or in part to the other monacolins, sterols (beta-sitosterol, campesterol, sigmasterol, and sapogenin), isoflavones, and monounsaturated fatty acids Red Yeast Rice extract (see Durington P, Bhatnager, et al, An omega-3 polyunsaturated fatty acid concentration administered for one year decreased triglycerides in simvastin treated patients with *CM. Heart* 2001:85(5) 544-548) This is a particular advantage since the lower dosage of Red Yeast Rice extract containing HMG-CoA reductase inhibitor contributes to reduced side effects as well.

Red Yeast Rice extract can be purchased as a nutritional supplement in the United States. Preferred sources include DRACO Natural Products (539 Parrott St., San Jose, Calif. 95112) Red Yeast Rice Extract 10:1, and the Thorne Research product, Choleast. Purchased Red Yeast Rice preferably should contain about 0.2 wt. % or more of monacolin K and about 0.5 wt. % or more of total monacolins.

The compositions of this invention can contain other ingredients besides the ingredients recited above. These include, but are not limited to, flavor agents, fillers, surfactants (e.g., polysorbate 80 and sodium lauryl sulfate), color agents including, e.g., dyes and pigments, sweeteners, antioxidants and additional ingredients.

Flavor Agents

Useful flavor agents include natural and synthetic flavoring sources including, but not limited to, volatile oils, synthetic flavor oils, flavoring aromatics, oils, liquids, oleoresins and extracts derived from plants, leaves, flowers, fruits, stems and combinations thereof. Useful flavor agents include, e.g., citric oils, e.g., lemon, orange, grape, lime and grapefruit, fruit essences including, e.g., apple, pear, peach, banana, grape, berry, strawberry, raspberry, blueberry, blackberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof, chocolate, cocoa, almond, cashew, macadamia nut, coconut, mint, chili pepper, pepper, cinnamon, vanilla, tooty fruity, mango and green tea. Mixtures of two or more flavor agents may also be employed. When a flavor agent is used, the amount employed will depend upon the particular flavor agent used. However, in general, the flavor agent can constitute from about 5% to about 50% by weight of the composition.

Color Agents

Useful color agents include, e.g., food, drug and cosmetic (FD&C) colors including, e.g., dyes, lakes, and certain natural and derived colorants. Useful lakes include dyes absorbed on aluminum hydroxide and other suitable carriers. Mixtures of color agents may also be employed. When a color agent is employed, the amount used will depend upon the particular color agent used. However, in general, the color agent can constitute from about 0.5% to about 5% by weight of the composition.

Sweetening Agent

Natural and/or artificial sweetening agents can also be added to the composition. Examples of sweeteners include sugars such as sucrose, glucose, invert sugar, fructose, and mixtures thereof, saccharin and its various salts (e.g., sodium and calcium salt of saccharin), cyclamic acid and its various salts, dipeptide sweeteners (e.g., aspartame), dihydrochalcone, and sugar alcohols including, e.g., sorbitol, sorbitol syrup, mannitol and xylitol, and combinations thereof. Natural sweeteners that can be employed include, but are not limited to, luo han, *stevia* or mixtures thereof. Luo han sweetener is derived from luo han guo fruit (*Siraitia grosvenorii*) that is mainly found in China. It is about 300 times sweeter by weight than sucrose. Luo han is commercially available from, e.g., Barrington Nutritionals (Harrison, N.Y.). *Stevia* is derived from a South American herb, *Stevia rebaudiana*. It can be up to about 300 times sweeter than sucrose. Because luo han and *stevia* have such a sweet taste, only a small amount need be used in the composition. When a sweetening agent is employed the amount used will depend upon the particular sweetening agent used. However, in general, the sweetening agent can constitute from about 0.0005% to about 30%, by weight of the composition. When a sweetener having a very sweet taste, such as luo han or *stevia*, is used, small amounts such as about 0.0005% to about 0.1% (for example about 0.005% to about 0.015% or about 0.002% to about 0.003%) by weight can be used.

Additional Ingredients

The compositions of the present invention can contain additional ingredients. Examples of such additional ingredients include, but are not limited to, vitamins, minerals and/or herbs.

As used herein, the term "vitamin" refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP), Coenzyme A (CoA), Coenzyme Q10 (CoQ10), pyridoxal phosphate, biocytin, tetrahydrofolic acid, coenzyme B12, lipoyllysine, 1-cis-retinal, and 1,25-dihydroxycholecalciferol. The term vitamin(s) also includes choline, carnitine, and alpha, beta, and gamma carotenes.

As used herein, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof. Compounds containing these elements are also included in the term "mineral."

As used herein, the term "herb" refers to organic substances defined as any of various often aromatic plants used especially in medicine or as seasoning. Thus, the term "herb" as used herein includes, but is not limited to, black currant, ginsing, ginko bilboa, cinnamon, and the like, and mixtures thereof.

Other ingredients that can be used include antioxidants, glucosamine and mixtures thereof.

The compositions of this invention are suitable for therapeutic and/or nutritional purposes in treating a subject in need of such treatment. As used herein, the term "subject" includes, but is not limited to, a non-human animal, such as a cow, monkey, horse, sheep, pig, chicken, turkey, quail, cat, dog, mouse, rat, rabbit, or guinea pig; and a human.

The amount of the composition of the invention that is effective will vary depending upon the condition being treated, and can be determined by standard clinical techniques. In addition, in vitro or in vivo assays can optionally be employed to help identify optimal dosage ranges. The precise dose to be employed will also depend on the relative amounts of the components of the compositions of the invention, route of administration, and the seriousness of the condition being treated and should be decided according to the judgment of the practitioner and each subject's circumstances. However, suitable effective dosage amounts for the compositions of the invention typically are at least about 2 grams per day, typically administered in the form of capsules containing at least about 1 gram of the composition per capsule. A typical dose should contain sufficient omega-3 acids or derivatives thereof to provide at least about 500 mg of a combination of EPA and DHA (or derivatives thereof).

The form in which the composition of the invention is administered to the subject is not critical. Typically, the composition is administered as a liquid or in a capsule. Typically, the composition is administered in the form of individual doses. As used herein, the term "dose" includes both the case where the Red Yeast Rice extract and the omega-3 compounds are administered together (such as in the form of a capsule containing both components), and the case where the Red Yeast Rice extract and omega-3 compounds are administered separately (but, typically, at essentially the same time). In some embodiments, the composition of the invention is administered in the form of a daily dose. However, depending on the severity of the condition being treated, this may not be required, and the period between administration of the doses may be longer than one day. In addition, the term "administer" includes both the case where a third party administers the dose to the subject and the case where the subject self-administers the dose.

EXAMPLES

In one embodiment a daily dosage is taken to reduce cholesterol and triglycerides, the dosage comprising 1.2 grams per day of Red Yeast Rice extract and 1700 mg of Nordic Naturals® ProOmega® fish oil supplement (which contains 70% Omega-3 oils which are 85.9% EPA and DHA, so that 1700 mg will supply 1000 mg/day of EPA and DHA). Here the weight ratio of fish oil to Red Yeast Rice extract is 1700/1200 (1.4:1). To make the mixture add 1200 weights of Red Yeast Rice extract to 1700 weights of fish oil. Add 58 weights (2%) of 70% silica bamboo and 87 weights (3%) of lysine and mix thoroughly to make a stable suspension. Fill gelatin capsules with the mixture such that an integral number of capsules dispenses 3045 grams of the mixture.

In some embodiments, a daily dose is taken, the dose comprising 1.2 grams per day of Red Yeast Rice extract and 3400 mg of fish oil such as ProOmega® fish oil supplement. Here the weight ratio of fish oil to Red Yeast Rice extract is 2.8 and will supply 2000 mg/day of EPA and DHA.

In some embodiments, a daily dose is taken, the dose comprising 2.4 grams per day of Red Yeast Rice extract and 3400 mg of fish oil. Here, the weight ratio of fish oil to Red Yeast Rice extract is 1.4.

In some embodiments, a daily dose is taken, the dose comprising 2.4 grams per day and 6800 mg of fish oil. Here, the weight ratio of fish oil to Red Yeast Rice extract is 2.8.

Although the present invention has been described in considerable detail with reference to certain versions thereof, other versions are possible. Therefore the spirit and scope of the appended claims should not be limited to the versions presented herein.

What is claimed is:

1. A composition comprising (1) EPA, a glyceride of EPA, or a mixture thereof, and DHA, a glyceride of DHA, or a mixture thereof, wherein at least about 60% w/w of (1) is in reesterified triglyceride form and the weight ratio of EPA in reesterified triglyceride form to DHA in reesterified triglyceride form is from about 1.4:1 to about 5:1; and (2) red yeast rice, wherein the red yeast rice is dispersed in (1) and comprises red yeast rice monacolin compounds, sterols, isoflavones and monounsaturated fatty acids, wherein the composition is formulated to provide a daily dose of (1) of from about 1000 mg to about 4000 mg and a daily dose of (2) of from about 1200 mg to about 2400 mg.

2. The composition of claim 1, wherein the red yeast rice comprises monacolin K and at least one other red yeast rice monacolin compound.

3. The composition of claim 2, wherein the red yeast rice comprises at least about 0.1 wt % monacolin K.

4. The composition of claim 2, wherein the red yeast rice comprises at least about 0.2 wt % monacolin K.

5. The composition of claim 2, wherein the red yeast rice comprises at least about 0.4 wt % monacolin K.

6. The composition of claim 1, wherein the red yeast rice comprises all of the monacolin compounds in red yeast rice.

7. The composition of claim 6, wherein the red yeast rice comprises at least about 0.4 wt % total red yeast rice monocolins.

8. The composition of claim 1, wherein at least about 80% of (1) is in the reesterified triglyceride form.

9. The composition of claim 1, wherein at least about 90% of (1) is in the reesterified triglyceride form.

10. The composition of claim 1, further comprising a dispersing agent.

11. The composition of claim 1, formulated into a gelatin capsule, wherein the daily doses of (1) and (2) are provided in an integral number of capsules.

12. The composition of claim 1, further comprising an antioxidant.

13. The composition of claim 12, wherein the antioxidant is selected from one or more of rosemary, vitamin E, astaxanthine, carnitine, ascorbyl palmitate, and tocopherols.

14. The composition of claim 1, further comprising other omega-3 polyunsaturated fatty acids or derivatives thereof.

15. The composition of claim 1, wherein, in the component (1) in reesterified triglyceride form, three fatty acid molecules, each independently selected from the group consisting of EPA and DHA moieties, are attached to a glycerol backbone.

16. The composition of claim 1, wherein the reesterified triglyceride form of component (1) is prepared by a process comprising removing fatty acids from a glycerol backbone of a triglyceride and then reesterifying EPA and/or DHA moieties onto the glycerol backbone.

17. The composition of claim 1, wherein the composition is formulated to provide a daily dose of (1) of about 1000 mg and a daily dose of (2) of about 1200 mg.

18. The composition of claim 1, wherein the composition is formulated to provide a daily dose of (1) of about 2000 mg and a daily dose of (2) of about 1200 mg.

19. The composition of claim 1, wherein the composition is formulated to provide a daily dose of (1) of about 4000 mg and a daily dose of (2) of about 2400 mg.

20. A method of reducing serum cholesterol, triglycerides, or both, comprising orally administering the composition of claim 1 to a human subject in need thereof in an amount effective to provide a daily dose of (1) of from about 1000 mg to about 4000 mg and a daily dose of (2) of from about 1200 mg to about 2400 mg.

\* \* \* \* \*